United States Patent [19]

Stiehl et al.

[11] Patent Number: 5,573,514
[45] Date of Patent: Nov. 12, 1996

[54] HOLDER FOR CARTRIDGE-NEEDLE UNIT

[75] Inventors: Mark A. Stiehl, Rochester; William A. Bergstresser, Prattsburgh, both of N.Y.; John J. Niedospial, Princeton Junction, N.J.

[73] Assignee: Sterling Winthrop Inc., New York, N.Y.

[21] Appl. No.: 610,511

[22] Filed: Mar. 4, 1996

Related U.S. Application Data

[63] Continuation of Ser. No. 128,934, Sep. 29, 1993, abandoned.

[51] Int. Cl.⁶ .......................................... A61M 5/32
[52] U.S. Cl. ........................... 604/198; 604/197; 604/240; 604/242
[58] Field of Search ................................... 604/263, 198, 604/195, 197, 110, 192, 187, 240, 243, 242, 181

[56] References Cited

U.S. PATENT DOCUMENTS

| | | | |
|---|---|---|---|
| 4,585,445 | 4/1986 | Hadtke . | |
| 4,810,248 | 3/1989 | Masters et al. | 604/192 |
| 4,932,940 | 6/1990 | Walker et al. | 604/110 |
| 4,994,045 | 2/1991 | Ramford | 604/263 |
| 5,019,051 | 5/1991 | Hake | 604/263 |
| 5,086,780 | 2/1992 | Schmitt | 604/198 |
| 5,226,894 | 7/1993 | Haber et al. | 604/198 |
| 5,232,457 | 8/1993 | Grim | 604/198 |

FOREIGN PATENT DOCUMENTS

| | | |
|---|---|---|
| 0485028 | 5/1992 | European Pat. Off. . |
| 9302728 | 2/1993 | WIPO . |
| 9305834 | 4/1993 | WIPO . |

*Primary Examiner*—Corrine M. McDermott
*Assistant Examiner*—Ronald K. Stright, Jr.
*Attorney, Agent, or Firm*—William J. Davis; Paul E. Dupont

[57] ABSTRACT

This invention relates to a holder for use in combination with a pre-filled cartridge-needle unit, the holder comprising a hollow body sized for housing the cartridge-needle unit therein, and means for permitting the body to move axially relative to the cartridge-needle unit. In one preferred embodiment, the distal end of the body is elliptical in cross section and the proximal end of the body is circular in cross section. In another preferred embodiment, the body comprises a pair of cam slots at the distal end and a pair or retaining slots at the proximal end, the slots being sized to accept a circumferential ring on the cartridge-needle unit and positioned to hold the cartridge-needle units in use and safe positions. The holder is easier to use and manufacture and reduces the susceptibility of health care workers to accidental needle strikes.

8 Claims, 12 Drawing Sheets

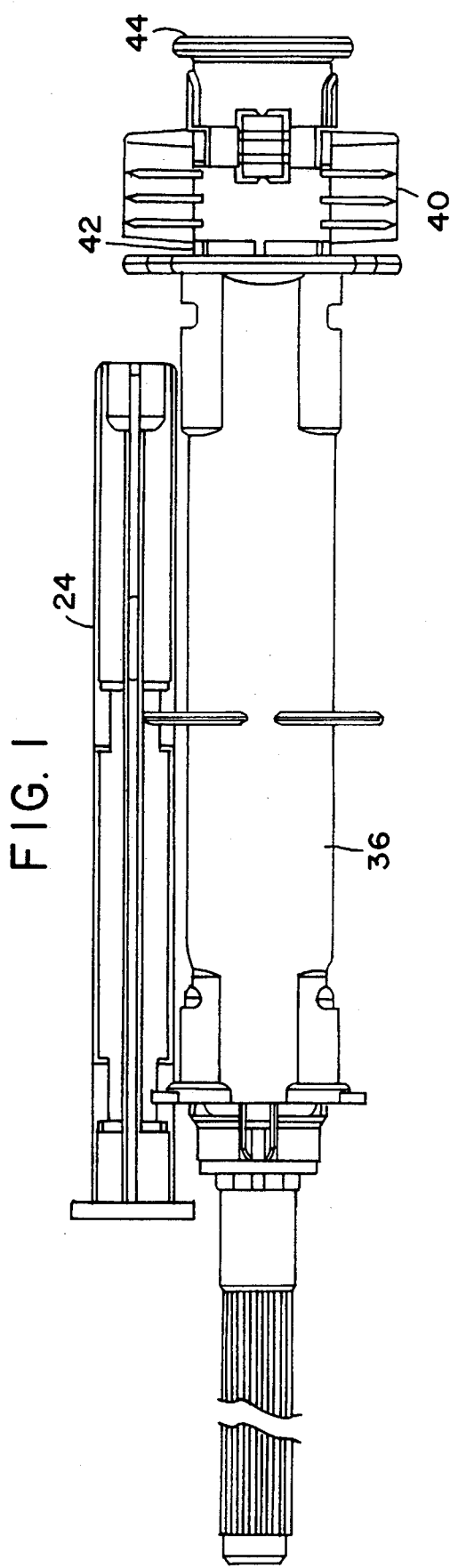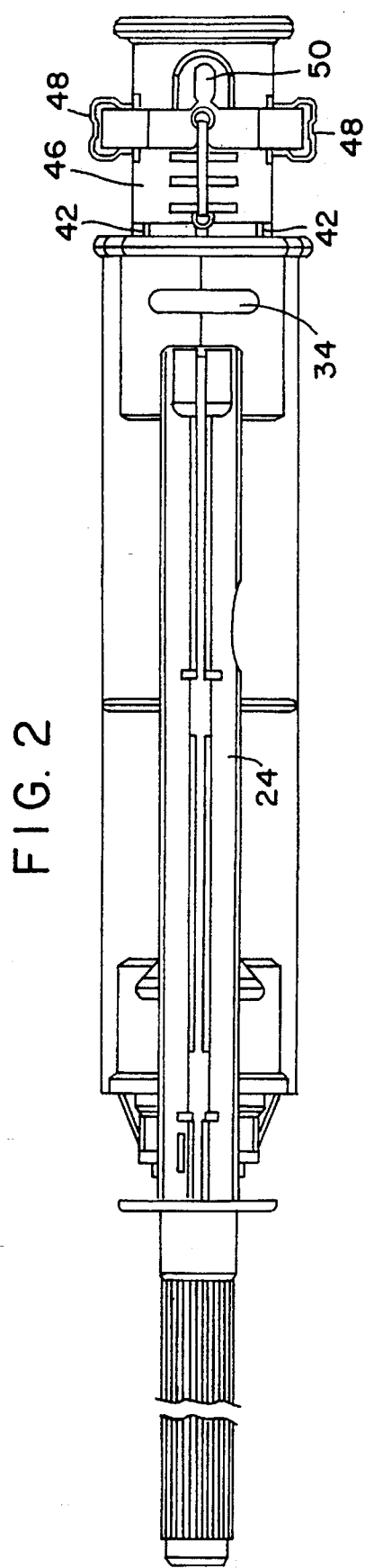

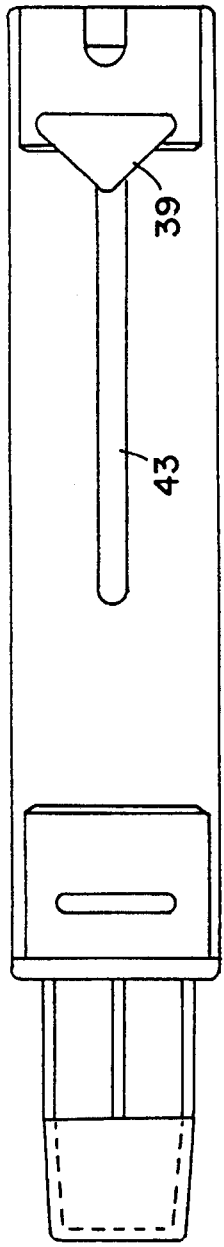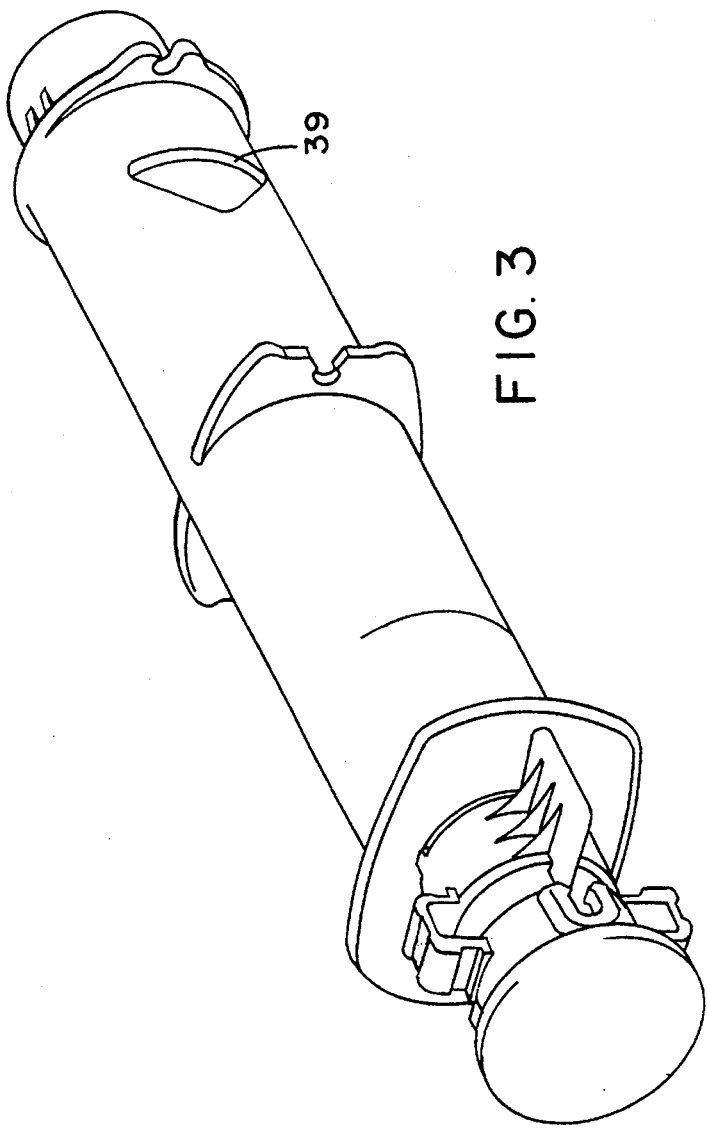

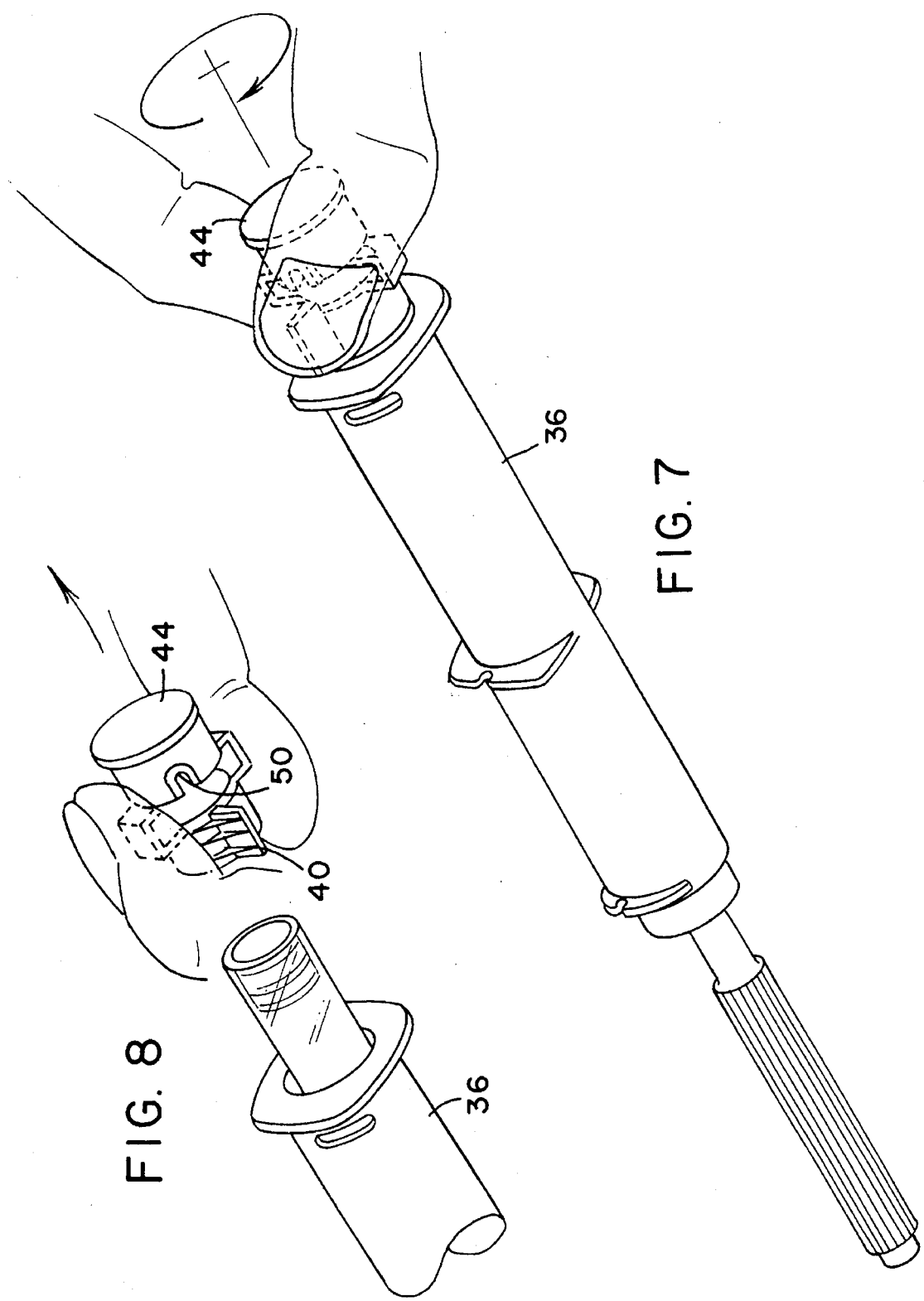

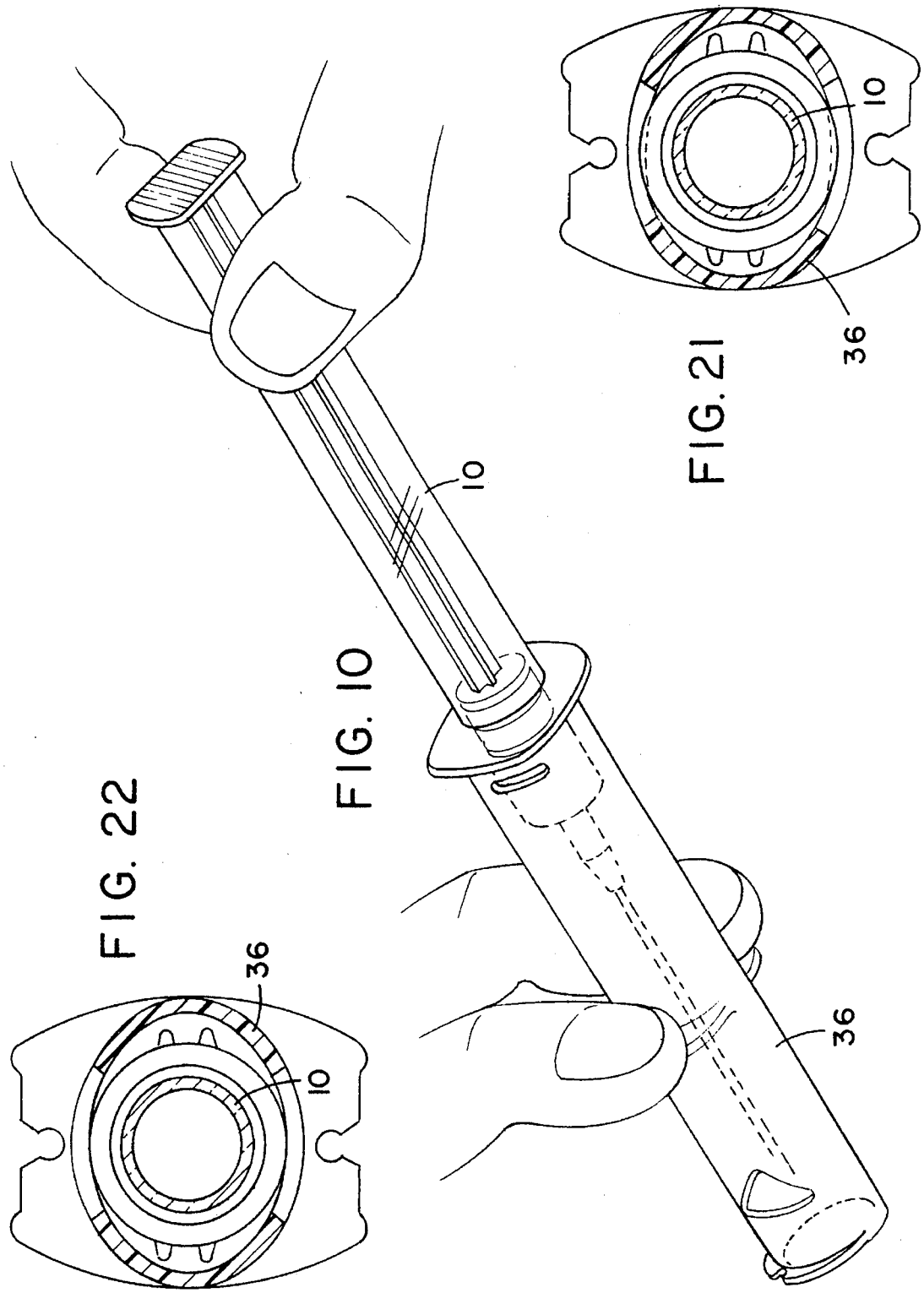

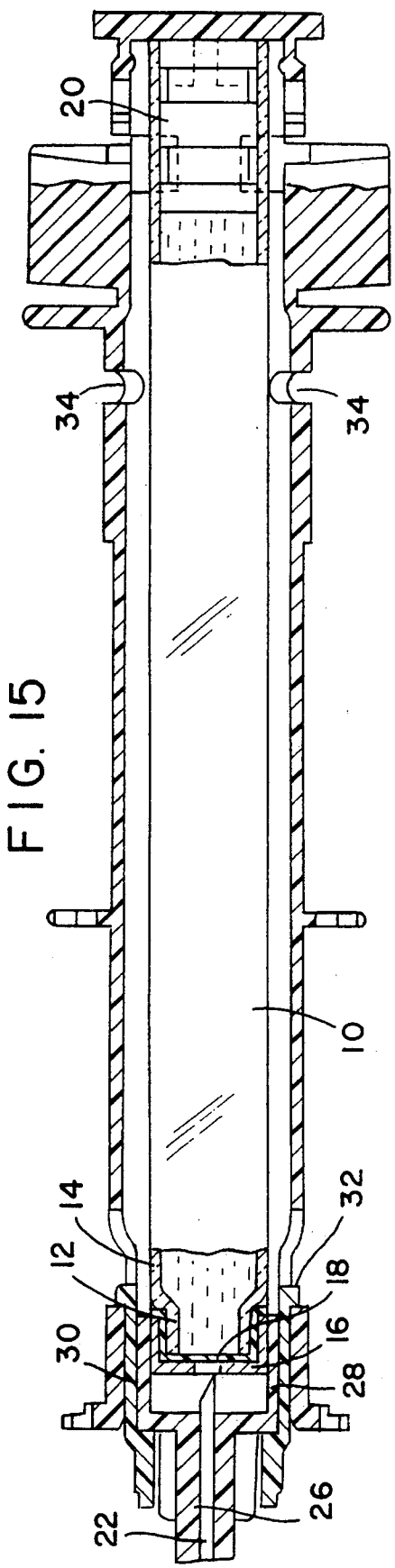
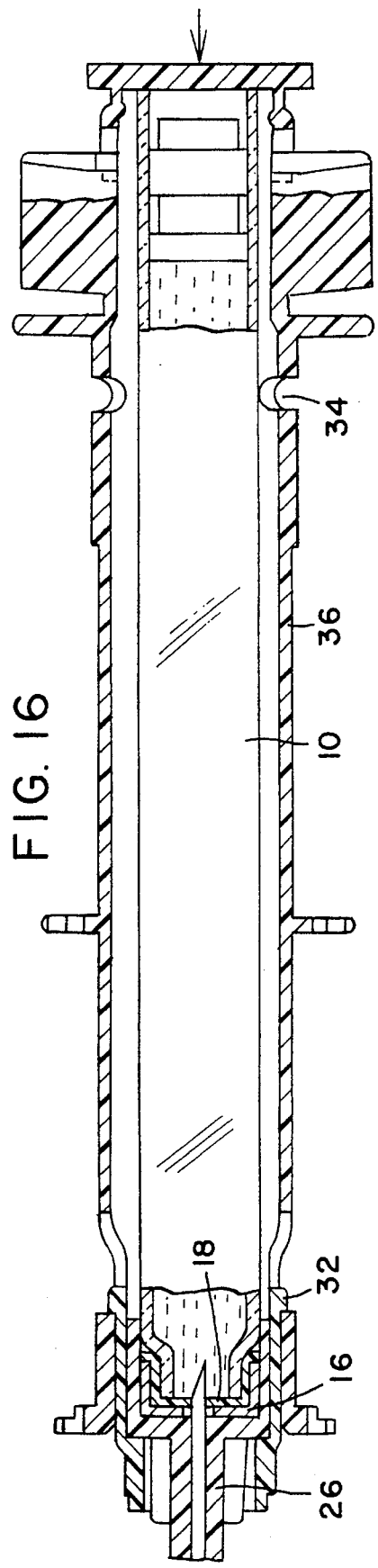

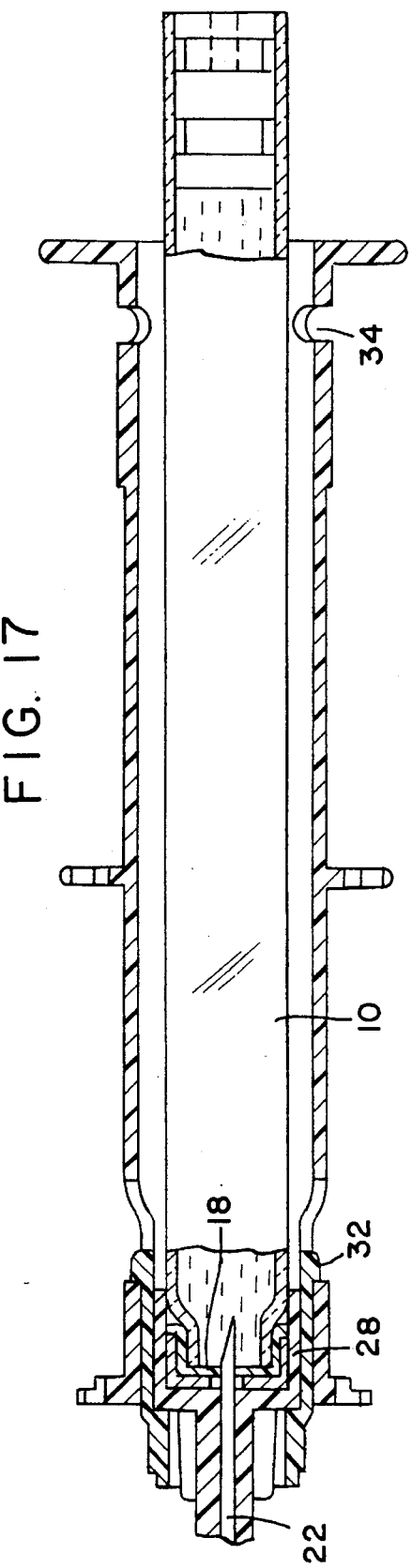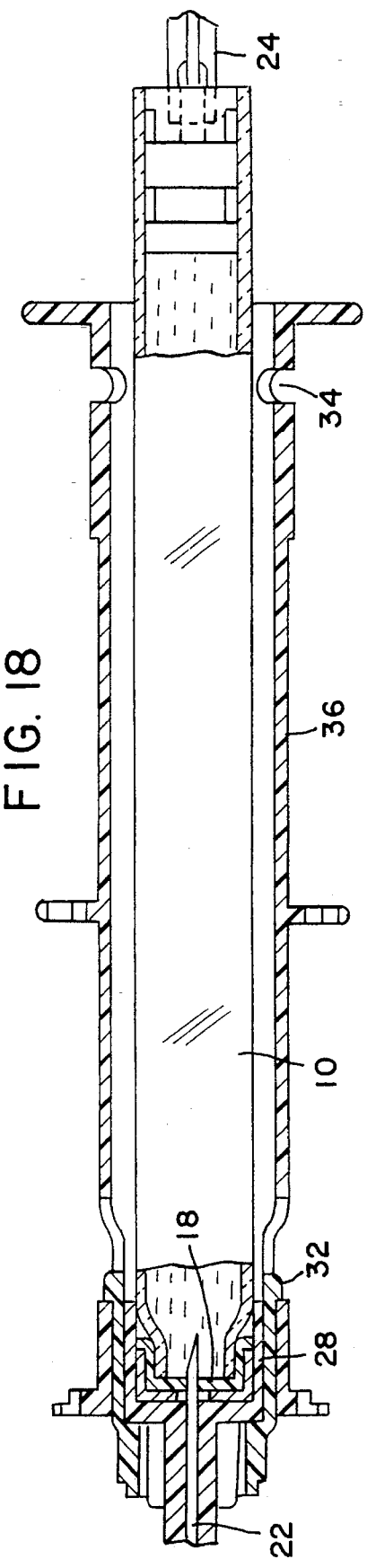

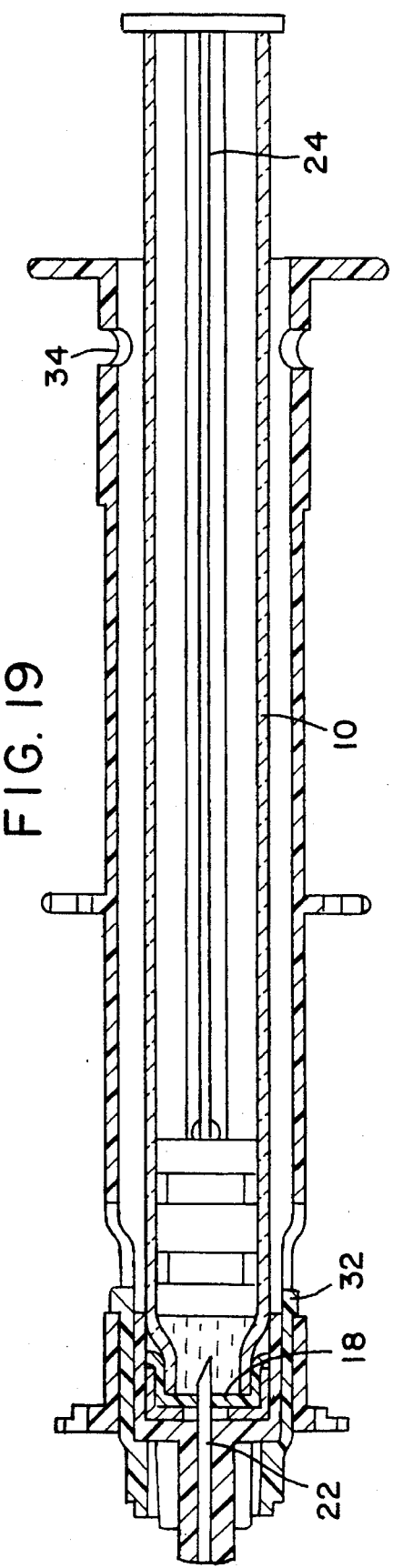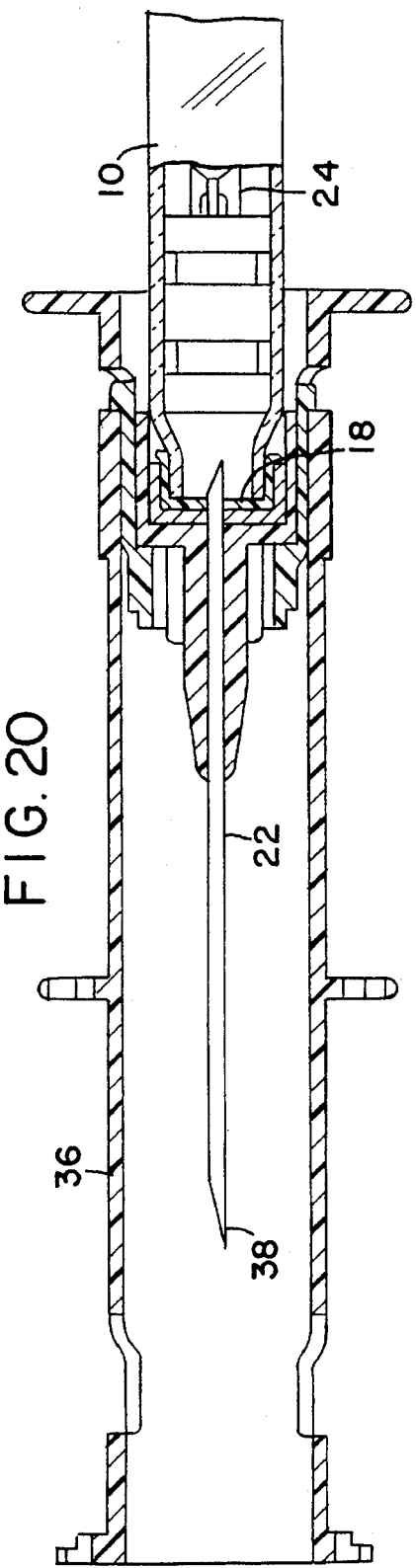
FIG. 19
FIG. 20

HOLDER FOR CARTRIDGE-NEEDLE UNIT

This is a continuation of application Ser. No. 08/128,934 filed Sep. 29, 1993, now abandoned.

BACKGROUND OF THE INVENTION

1. Field of the Invention

This invention relates to a holder for pre-filled cartridge-needle units.

2. Description of the Prior Art

Disposable medicament-containing cartridge needle units for use in conjunction with reusable hypodermic syringe holders are well known in the art and are in widespread commercial use such cartridges conventionally feature a cylindrical body closed at the proximal end with a flexible plunger slidable within the bore of the cartridge and closed at the distal necked-down end with a septum secured to the cartridge by a crimped-on aluminum collar. The necked-down distal end conventionally is fitted with a needle hub/needle/needle guard assembly. Such cartridge-needle units are available from Sanofi Winthrop Pharmaceuticals under the Carpuject® trademark.

In use, the cartridge-needle unit must be activated, i.e., the proximal end of the needle cannula must penetrate the sealed septum such that communication is achieved between the fluid and the proximal end of the needle. Some cartridge-needle units are sold in an activated form. Others must be activated by the user. When user activated cartridge-needle units are used in conjunction with conventional reusable syringe holders of the type described, for example, in Hadtke, U.S. Pat. 4,585,445 and in EP-A 485,028, this is accomplished when the health care worker advances the cartridge through the holder by rotating a clamping element.

Many holders, including the above-referenced reusable holders, enable the user to avoid handling the cartridge-needle unit when the needle unit is exposed. Nevertheless, health care workers are especially susceptible to accidental and potentially infectious, and indeed, on occasion, possibly fatal, needle strikes due to the careless handling and/or disposing of the cartridge-needle unit after use. The consequences to health care workers of strikes from needles contaminated with various infectious diseases such as hepatitis or AIDS can be particularly severe. The frequency of such accidental needle strikes in the United States is surprisingly great, and has been estimated to be approximately one million strikes per year. Moreover, the cost to health care organizations for the testing of health care workers accidentally stricken by used needles is a significant burden on health care costs. Therefore, it would be desirable to further protect health care workers by providing systems which reduce the possibility of accidental needle strikes.

To this end, it has been suggested to provide a hollow body to house the cartridge-needle unit, such that the needle can be exposed for use and then withdrawn into the body for safety. For example, WO 93/02728 describes disposable, i.e., single use, holders which can be used in conjunction with cartridge-needle units. However, this system comprises a body featuring one or more radially inwardly extending spring fingers near the plunger end of the body which engage the hub of the needle assembly and keep the needle assembly from being withdrawn from the body section. Such spring fingers are difficult to mold and require a folding step during assembly. Additionally, when folded into position, the spring fingers create an abrupt ledge which, if contacted by the cartridge-needle unit during the assembly process, can cause premature activation of the assembled unit, thus rendering the unit defective. WO 93/05834 describes another such system featuring a holder containing a radially deformable body having an elliptical cross-section. However, full elliptically shaped holders tend to inadequately support the cartridge-needle unit and cause alignment problems during manufacture and/or assembly and safety problems during use. To reduce such problems WO 93/05834 proposes the use of spring fingers, but such designs suffer from the problems discussed above. Further, holders featuring deformable bodies require that the users place their fingers close to an exposed needle with no protection during deformation. Consequently, these systems are less than fully satisfactory from a commercial standpoint.

In addition, existing safety syringe systems often are not economical to manufacture and/or assemble in large quantities. This is especially true when the syringe system is intended to be disposable.

It would be desirable to provide a holder for use with a cartridge-needle unit which enables the unit to be assembled and used safely and easily and which reduces the susceptibility of health care workers to accidental needle strikes.

SUMMARY OF THE INVENTION

We have discovered an improved disposable holder for use in combination with a cartridge-needle unit which is easy to use and manufacture and which reduces the susceptibility of health care workers to accidental needle strikes.

More specifically, in accordance with this invention, there is provided a holder for use in combination with pre-filled cartridge-needle units, the holder comprising a hollow body sized for housing the cartridge-needle unit therein, and means for permitting the body to move axially relative to the cartridge-needle unit. In one preferred embodiment, the distal end of the body is elliptical in cross-section and the proximal end of the body is circular in cross section.

In another preferred embodiment, the cartridge-needle unit contains a circumferential ring and the body comprises a pair of cam slots at the distal end and a pair of retaining slots at the proximal end, the slots being sized to accept the circumferential ring and positioned to hold the cartridge-needle unit in use and safe positions.

It is an advantageous feature of this invention that a holder is provided for cartridge-needle units which is easier for the health care worker to use.

It is another advantageous feature of this invention that a holder is provided for cartridge-needle units which reduces the susceptibility of health care workers to accidental needle strikes.

Still another advantage of this invention is that a disposable, i.e., single use, holder is provided for commercially available cartridge-needle units.

Yet another advantageous feature of this invention is that a holder is provided which can be easily and economically manufactured and assembled.

Other advantages will become readily apparent upon reference to the following descriptions of preferred embodiments when read in light of the accompanying drawings.

BRIEF DESCRIPTION OF THE DRAWINGS

FIGS. 1 and 2 are front and side views of a preferred embodiment of the holder of this invention and an associated plunger rod.

FIG. 3 is a perspective view of a holder featuring triangular cam slots.

FIG. 4 depicts a holder featuring side grooves and cam slots.

FIGS. 7 and 8 are perspective views of a user removing the cap from the body of the holder.

FIG. 10 is a perspective view depicting a user grasping the body behind the retraction finger guards and pulling the cartridge-needle unit such that the needle is withdrawn into the body of the holder.

FIGS. 15 and 16 are partial cross-sectional front views illustrating a holder of this invention and an associated cartridge-needle unit before and after activation.

FIGS. 17 and 18 are partial cross-sectional front views depicting the holder of FIG. 1 after removal of the cap, before and after attachment of the plunger rod to the plunger.

FIG. 19 is a cross-sectional front view of a holder and cartridge-needle unit having the plunger in a fully expulsed position.

FIG. 20 is a partial cross-sectional front view of a needle withdrawn into the body of a holder.

FIGS. 21 and 22 are cross-sectional top views illustrating the body in undeformed and deformed states, respectively.

DESCRIPTION OF PREFERRED EMBODIMENTS

Figures 5, 6:
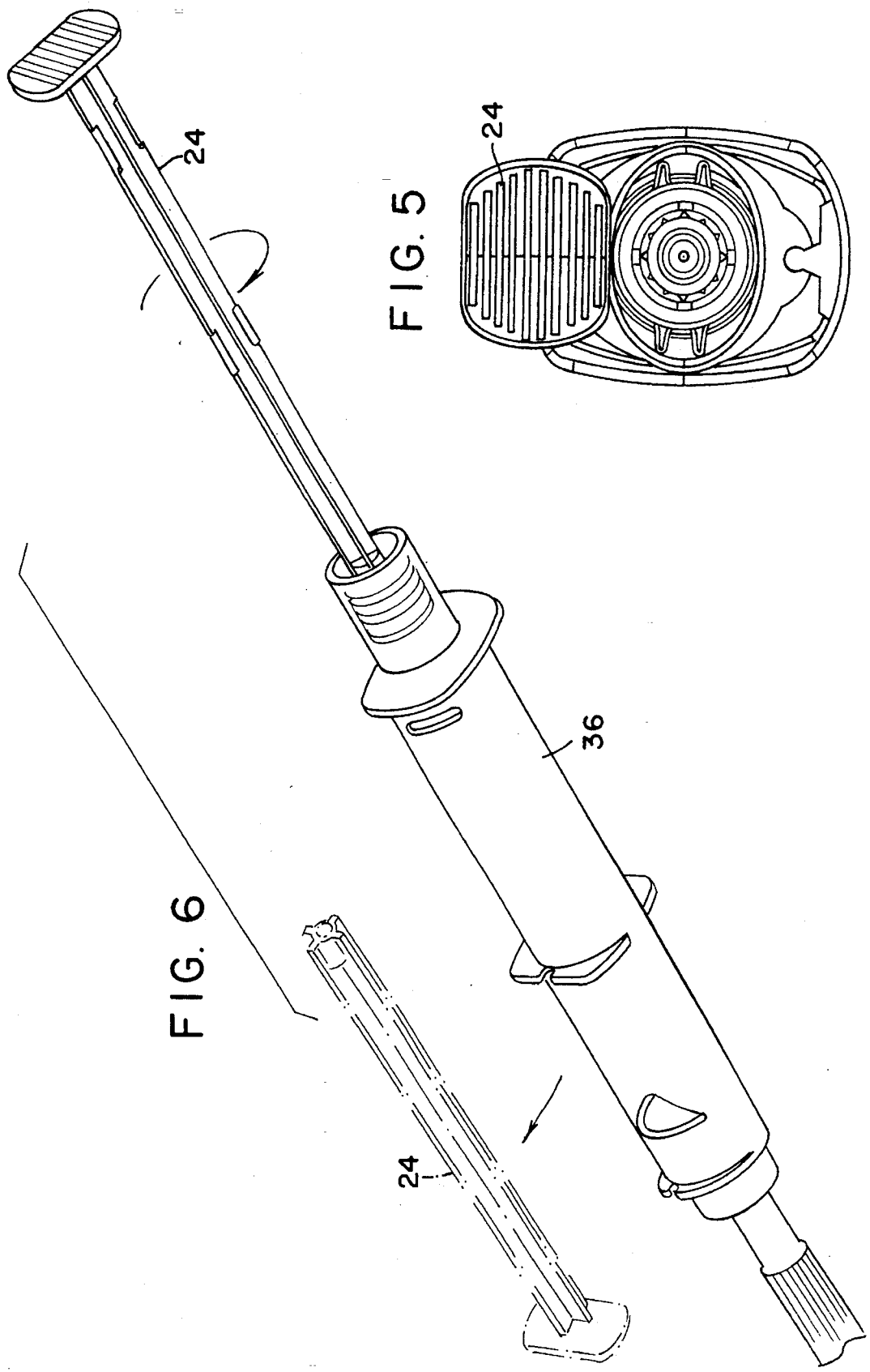
FIG. 5 is a top view of the holder depicted in FIG. 1.
FIG. 6 is a perspective view illustrating a plunger rod unsnapped from the body of the holder and the motion used to attach the plunger rod to the plunger.

In a preferred embodiment, the holder of this invention is used in conjunction with a prefilled cartridge-needle unit. The prefilled cartridge-needle unit can be of a conventional design and can include a hollow, transparent body, typically fabricated of glass, which is prefilled with a supply of fluid medication or the like. Such cartridge-needle units currently are in widespread commercial use. With reference to FIG. 15, the cartridge 10 includes head portion 12 and a cylindrical body 14 which are coextensively joined together at a relatively narrow neck. A metallic end cap 16 covers a sealed septum 18 which extends across the distal end of the cartridge to prevent contamination and leakage of the fluid contents. Plunger 20 is sized to be received in and slidable axially and reciprocally through the interior of the cartridge. The plunger is formed from a relatively dense resilient material, e.g., rubber, and can be moved distally through the cartridge for expulsing the fluid contents of the cartridge via distal end 38 (FIG. 20) of needle cannula 22 so as to project outwardly from the end thereof. The screw-threaded post can be mated to screw-threadable plunger rod 24, FIGS. 1 and 6, of an associated holder to complete a plunger assembly for controlling the movement of the plunger through the interior of the cartridge. The plunger rod can comprise a pluralility of ribs extending longitudinally on the interior surface of the cavity adapted to be threaded onto the post, such as is described in U.S. patent application Ser. No. 08/128,933 entitled PLUNGER ROD FOR CARTRIDGE NEEDLE UNIT filed on Sep. 29, 1993 now abandoned, the disclosure of which is hereby incorporated by reference in its entirety. Such a preferred plunger rod is depicted in detail in FIGS. 11–14. An advantage of such design is that the plunger can be manufactured by conventional injection molding techniques. It is contemplated that other means known in the art can be employed for attaching the rod to the plunger stem.

The necked-down distal end of the cartridge-needle unit can be fitted with a needle hub/needle/needle guard assembly. Needle hub 26 (FIG. 15) can be attached to the cartridge by snapping sleeve 28 over the distal end of the cartridge to engage the metallic end cap.

The cartridge-needle unit can be provided with collar 30 extending from the needle end. The collar has a circumferentially extending adapter ring 32 sized to engage specifically positioned pairs of retaining slots 34 formed in the body. In a preferred embodiment, the collar is of the type depicted in FIGS. 23–26 and described in commonly assigned U.S. Pat. application Ser. No. 08/129,932 entitled COLLAR FOR CARTRIDGE-NEEDLE UNIT, filed on Sep. 29, 1993,now abandoned, the disclosure of which is hereby incorporated by reference in its entirety. Alternatively, the cartridge-needle unit can be provided with an integral adapter ring, e.g., as part of the needle hub.

The holder of this invention comprises hollow body 36 (FIG. 1) sized for housing the cartridge-needle unit therein, and means for permitting the body to move axially relative to the cartridge-needle unit. In one preferred embodiment, the holder comprises a hollow body having a substantially elliptical cross-section 31 (FIG. 5) at the distal end and a substantially circular cross-section 33 at the proximal end. The elliptical distal end preferably is squeezably deformable. The circular cross-section preferably is sized to surround the cartridge-needle unit. Such a holder featuring a so called "transition body", i.e., a body which has an elliptical cross-section at the distal end and a circular cross-section at the proximal end, provides significant advantages compared to the prior art designs described above. For example, cartridge-needle units tend to be unstable in a holder featuring a body which is solely elliptical in cross-section, because they are inadequately supported. The instability of such systems, in practice, can lead to unacceptable safety risks. Further, the holder of this invention is much easier to manufacture and/or assemble than the prior art holders. For example, elliptically shaped bodies require alignment during assembly. Prior art holders featuring inwardly extending spring fingers are difficult to mold and require "folding" during assembly. In addition, spring fingers increase the friction between the cartridge and holders and thus the force required to activate the cartridge and/or retract the cartridge into the body after use. On the other hand, the transition to a circular cross-section at the proximal end of the holder of this invention facilitates alignment of the cartridge-needle unit both during assembly of the syringe system and during use. Moreover, the circular cross-section can be sized such that it does not permit the cartridge-needle unit to be pulled through the proximal end of the holder during retraction, thus avoiding a risk to the user's safety. The circular shaped body can effectively block the circumferential ring from further axial movement in the proximal direction. Indeed, the present invention permits the spring fingers and problems associated therewith of prior art designs to be totally eliminated. Finally, a body having a circular shaped proximal end facilitates use of a cap intended to be threaded onto the proximal end of the body.

Figure 27:
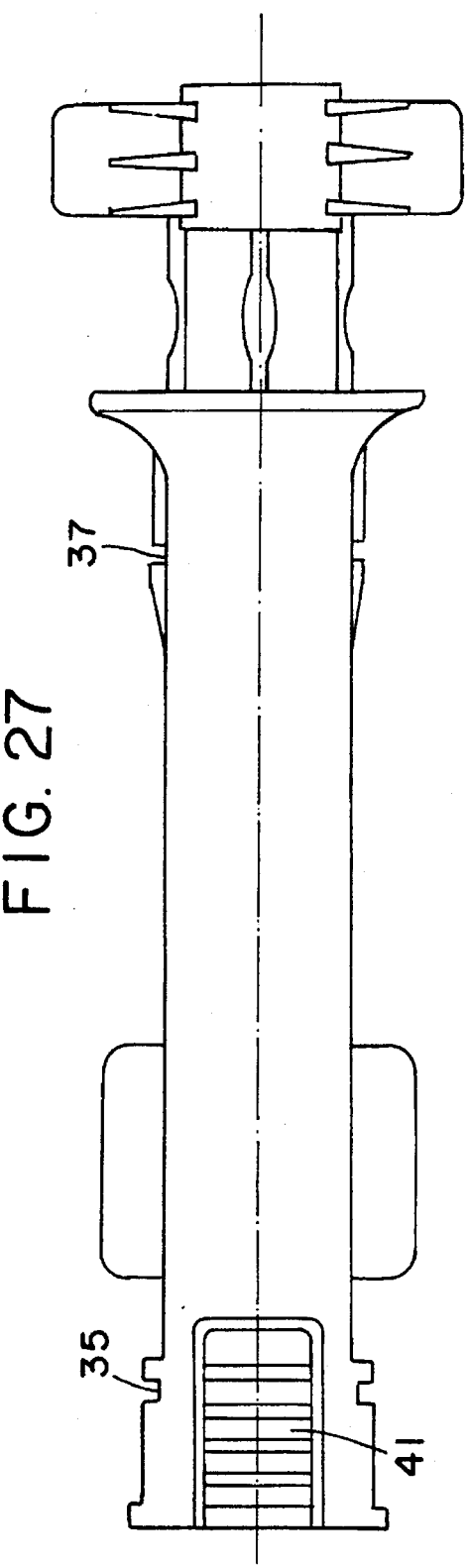
FIG. 27 is a side view of a holder of this invention featuring retaining slots and squeeze pads.

The body can comprise one or more retaining slots 35 (FIG. 27) at the distal end thereof and one or more retaining slots 37 at the proximal end thereof. The slots are sized to accept the circumferential ring of the cartridge-needle unit. The outer circumference of the adapter ring can enter the retaining slots when the body is in its normal undeformed condition. To disengage the adapter ring from the retaining slots, the user squeezes the body opposite the retaining slots, i.e., inwardly along the major axis of the ellipse, thereby permitting the body to move axially with respect to the cartridge-needle unit. The retaining slots are preferably positioned so that the cartridge-needle unit is held in place in a use position and in a safe position, i.e., such that the tip of the needle cannula is within the interior of the body.

Figure 9:
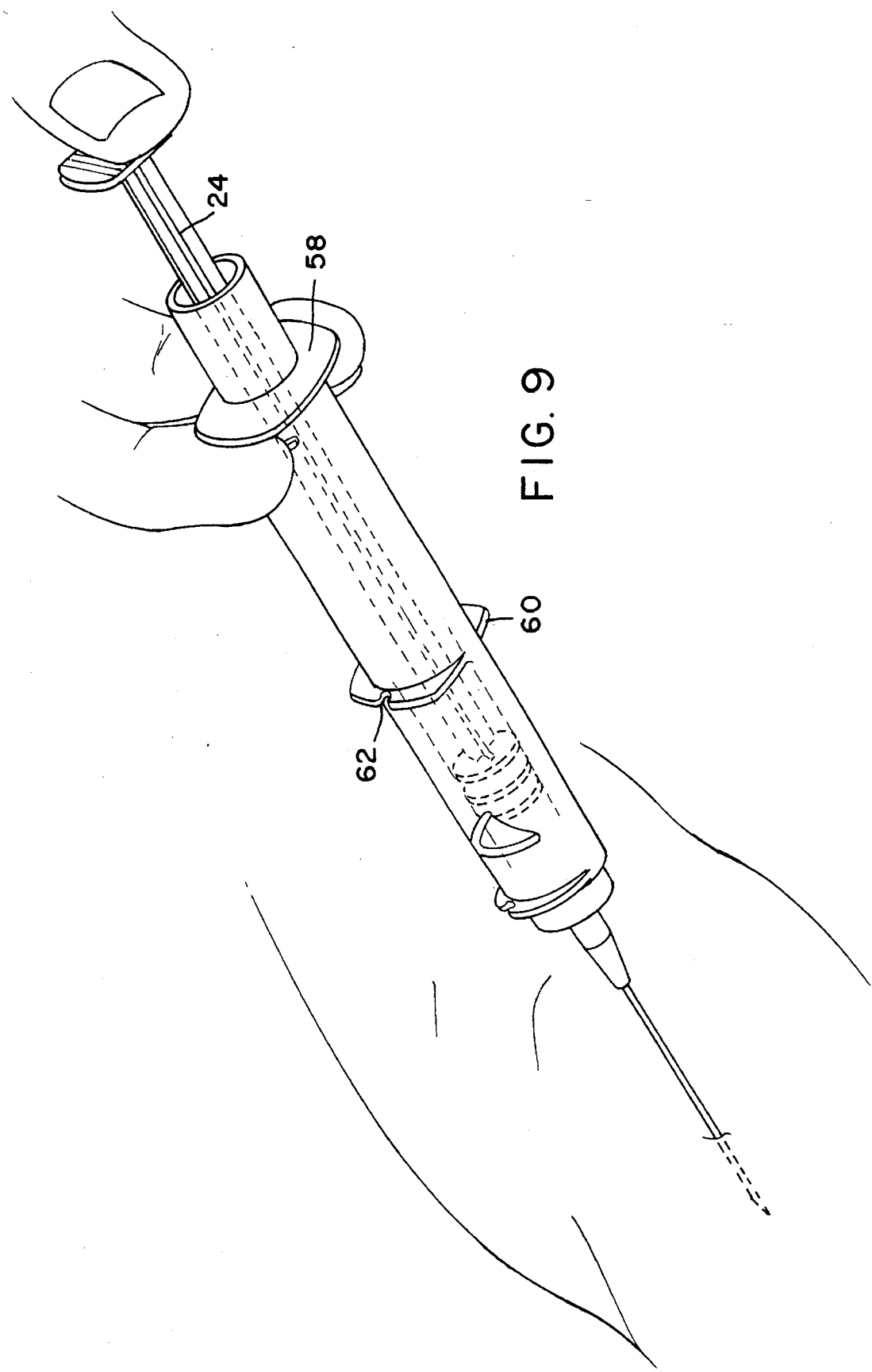
FIG. 9 is a perspective view depicting a needle, an injection site and a user applying force to the plunger rod via the thumb pad.
Figure 12:
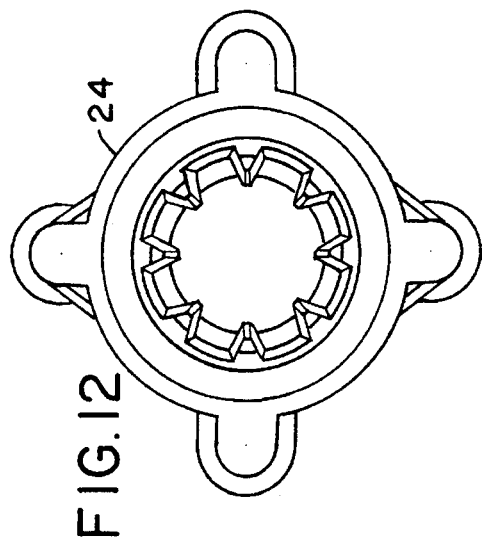
FIGS. 11 and 12 are perspective and bottom views of a preferred plunger rod for use with the holder of this invention.
Figure 14:
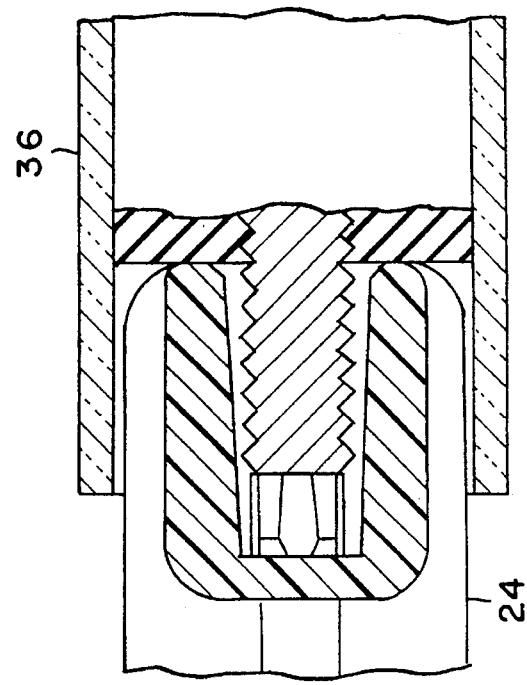
FIGS. 13 and 14 are cross-sectional views depicting the plunger rod of FIG. 11 before and after attachment to a plunger.
Figure 11:
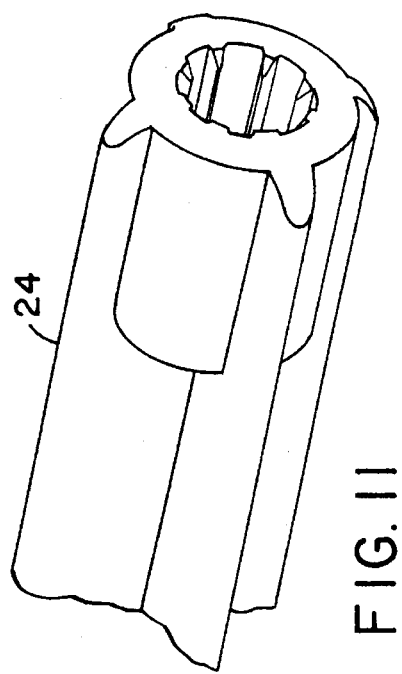
Figure 13:
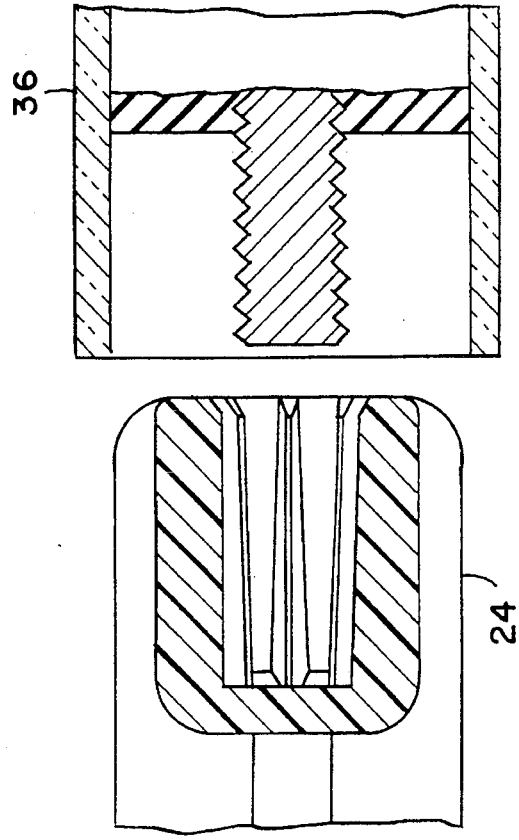
Figure 23:
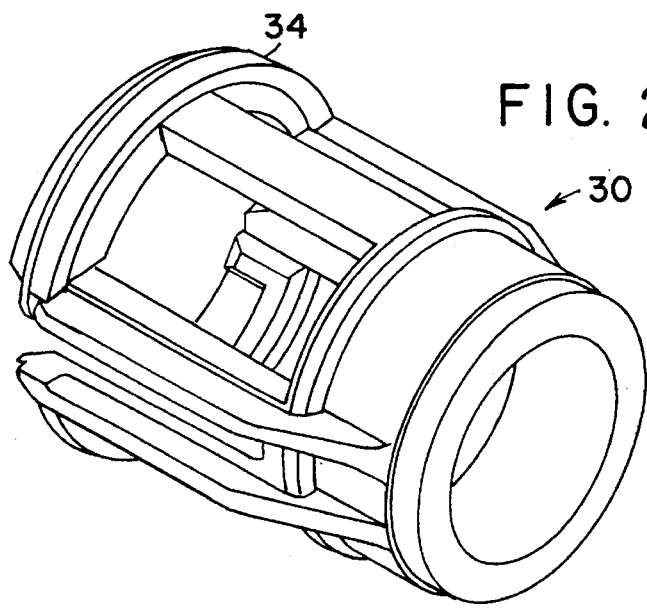
FIGS. 23–26 are perspective, top and cross-sectional front and side views of a collar, i.e., a cartridge adapter, for use with a cartridge-needle unit in a preferred embodiment of the invention.
Figure 24:
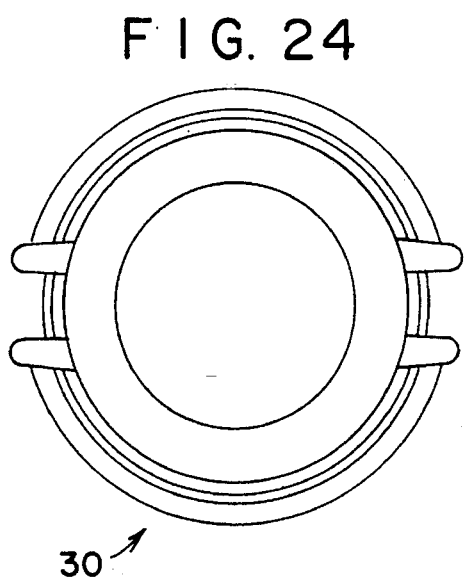
Figure 25:
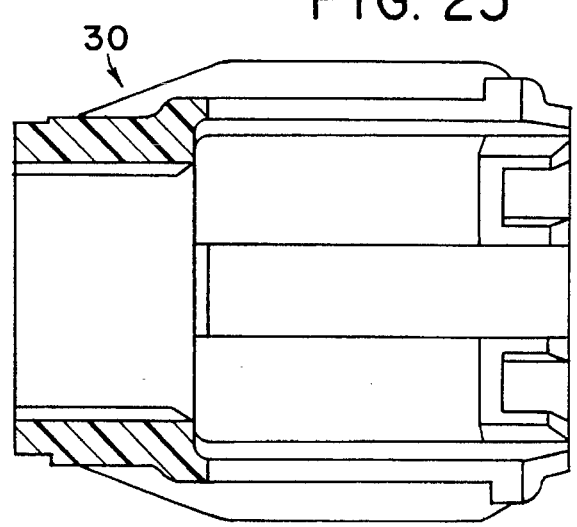
Figure 26:
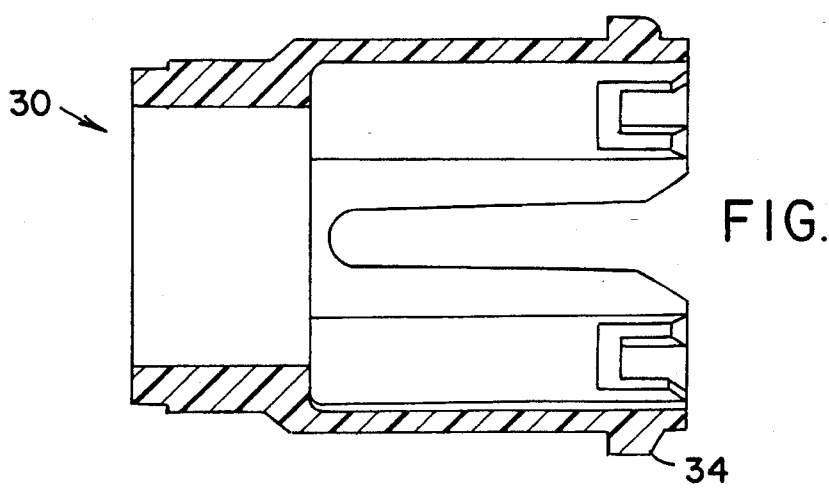
Figure 28:
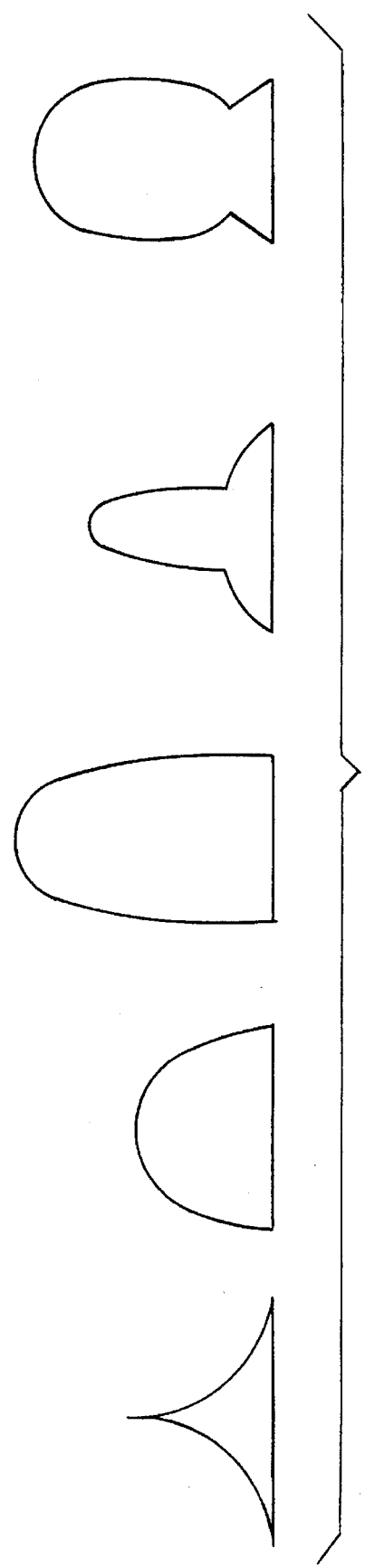
FIG. 28 illustrates exemplary useful shapes for the cam slots.

In another preferred embodiment, the body comprises a pair of cam slots 39 (FIGS. 1–4) disposed within the distal end of the body. In a preferred embodiment, the cam slots are triangular in shape. This shape works well and is easy to manufacture. However, any shape that does not have a shelf for the collar to strike against may work. Exemplary useful shapes are depicted in FIG. 28. It is a particular advantage that cam slots are self activating and do not require user interface. In other words, cam slots do not require that the user squeeze the body in order to release the adapter ring from the slots. This is a particular advantage both from the standpoint of ease of use and user safety. When cam slots are present, health care workers are not required to squeeze the body to free the adapter ring to permit the body to move. Systems requiring the health care worker to squeeze the body can be disadvantageous inasmuch as they require the health care worker to place his finger close to the needle during the squeezing process and then push the body of the holder forward with the same hand, thus posing a possibility of a risk that the hand can slide off the body of the holder and onto the exposed used needle. In addition to the safety advantage of not requiring one hand of the user to be near the used needle, cam slots enable the free hand to be used in conjunction with retraction finger guards 60 (FIGS. 9 and 10) to facilitate the safe retraction of the cartridge-needle unit into the body of the holder.

When the distal end of the body is elliptical and squeezably deformable, it is preferred that a pair of squeeze pads 41 (FIG. 27) be disposed on the distal end of the body opposite the retaining slots and along the major axis of the ellipse. The squeeze pads are advantageous in that they guide the user to squeeze the elliptical deformable distal end of the body in the correct orientation relative to the body and retaining slots, enabling the circumferential ring to be released from the retaining slots. Further, the squeeze pads reduce the force required to be exerted by the user to release the circumferential ring from the retaining slot. Additionally, the squeeze pads can help reduce the tendency for the health care worker's hand to slip off the body toward the exposed needle during retraction of the used cartridge-needle assembly into the body. The body can comprise one or more axial grooves 43 which facilitate the axial sliding movement of the body relative to the cartridge-needle unit during retraction by increasing the flexibility of the body and/or decreasing the frictional force between the body and the cartridge-needle unit.

In a preferred embodiment of this invention, the proximal end of the cartridge-needle unit is provided with a cap. The cartridge-needle unit, if activable, preferably can be activated by application of force to the cap. The force can be applied to the cap directly, e.g., by twisting the cap, and/or indirectly, e.g., through a lever element. The cap can be embodied in several different forms. For example, cap 40 (FIG. 1) is formed integrally with the body and attached to the proximal end thereof by one or more, preferably a plurality of, frangible tethers 42. The cap comprises activation pad portion 44 attached to the portion of the cap containing twist tabs 46 by non-frangible plastic connectors 48 (FIG. 2). By selecting an appropriate distance between the pad and tab portions, the cartridge-needle unit can be activated by application of force to the cap, i.e., by pressing the pad portion until it becomes fully seated. The pad portion can include notches 50 which engage the twist tabs to facilitate activation. The twist tabs facilitate application of a sharp twisting motion to the cap by the user in order to fracture the tethers, enabling removal of the cap. An advantage of this embodiment is that the cap is tamper-evident. When a plurality of tethers are present, one tether can be designed to be stronger than the others, so that the strong tether remains intact when the others are fractured. Accordingly, the cap need not be disposed of as a separate piece.

In another embodiment, the cap comprises a plurality of frangible tethers and a lever element, which can be lifted by the user and rotated about a pivot point to cam the cartridge-needle unit forward and activate the cartridge. After activation, the lever provides force sufficient to fracture the frangible tethers, thus separating the cap from the body. In another embodiment, the cap can be provided with female threads and the body can be provided with male threads attached through frangible tethers. The female threaded cap is adapted to be threaded onto the male threads of the body.

In a preferred embodiment, the holder is provided with finger flange 58 (FIG. 9) to facilitate the injection process. When the holder comprises cam slots, it is particularly preferred that retracting finger guards 60 be provided to facilitate retraction of the cartridge-needle unit into the holder in a safe and reliable manner. The body can be provided with retention feature 62 which permits the plunger rod to be attached via a snap fit to the holder.

The syringe holder of this invention can be fabricated of any suitable material including metals and plastics. However, it is well adapted to be made of plastic. In particular, the holder and associated collar can be fabricated of rigid plastic using known precision injection molding techniques. Suitable plastics include polypropylene, polystyrene, polycarbonates, ABS (clear or opaque), nylon, acetals, polyethylene or polyester. The material can include a slip agent or lubricant to facilitate the sliding motion of the body with respect to the cartridge-needle unit. A preferred slip agent is PETRAC SLIP-EZE OLEAMIDE, a fatty amide commercially available from Synpro, Cleveland, Ohio.

In use, the holder of this invention operates in conjunction with conventional cartridge-needle units for administration of an injection as follows. First, the plunger rod can be unsnapped from the body of the syringe assembly. If necessary, the cartridge-needle unit can be activated, e.g., by applying force to the cap. The cap is then removed, for example, by grasping the twist tabs and applying a sharp twisting motion, to expose the plunger. The associated plunger rod can then be attached to the exposed plunger, e.g., by threading it onto the post and turning clockwise. Next, the needle guard is removed to expose the needle cannula. The needle is inserted into an injection site and an axially and distally directed force is applied by the health care worker to the plunger rod via the thumb pad. The distal force is transferred from plunger rod to plunger, to drive the plunger through medicament-containing cartridge-needle unit and to thereby expulse the fluid contents of the cartridge via the needle cannula into the injection site. After the injection is administered, the needle cannula is removed from the injection site. Subsequently, the body can be squeezably deformed, or, when cam slots are present, grasped behind the retraction finger guards, and the cartridge-needle unit can be pulled proximally back by the user such that the adapter ring is accepted by the distal retaining slots and the exposed needle is withdrawn into and held within the body of the holder, thus significantly reducing the possibility of accidental needle strikes. The holder-used cartridge-needle unit combination can be disposed of in an appropriate manner.

The invention has been described in detail with particular reference to certain preferred embodiments thereof, but it will be understood that variations and modifications can be effected within the spirit and scope of the invention.

What is claimed is:

1. A holder for use in combination with a pre-filled cartridge-needle unit, said holder comprising:

a hollow body sized for housing the cartridge-needle unit therein having proximal and distal ends said body comprising a pair of squeeze pads disposed on the distal end thereof; and means for permitting said body to move axially relative to the cartridge-needle unit between use and safe positions;

wherein the distal end of said body is elliptical in cross-section, said ellipse having a major axis substantially longer than its minor axis, and the proximal end of said body is circular in cross-section and said body is tapered from said elliptical end to said proximal end and comprises a first pair of retaining slots at the distal end thereof and a second pair of retaining slots at the proximal end thereof, said slots being sized to accept a circumferential ring of the cartridge-needle unit and positioned to hold the cartridge-needle unit in use and safe positions.

2. The holder of claim 1 wherein said first pair of retaining slots are cam slots.

3. The holder of claim 2 wherein said cam slots are triangular in shape.

4. The holder of claim 1 wherein the distal end of said body is squeezably deformable.

5. The holder of claim 1 further comprising retraction finger guards disposed on said hollow body approximately midway between said proximal and distal end.

6. A holder for use in combination with a pre-filled cartridge-needle unit having a circumferential ring, said holder comprising:

a hollow body sized for housing the cartridge-needle unit therein having proximal and distal ends, said body comprising a pair of squeeze pads disposed on the distal end thereof; and means for permitting said body to move axially relative to the cartridge-needle unit between use and safe positions;

wherein said body comprises a pair of triangular cam slots at the distal end thereof and a pair of retaining slots at the proximal end thereof, said slots being sized to accept the circumferential ring and positioned to hold the cartridge-needle unit in use and safe positions and wherein the distal end of said body is elliptical in cross section, said ellipse having a major axis substantially longer than its minor axis and the proximal end of said body is circular in cross section and said body is tapered form said distal elliptical end to said proximal circular end.

7. The holder of claim 6 wherein said body comprises an axial groove to facilitate retraction.

8. The holder of claim 6 further comprising retraction finger guards disposed on said hollow body approximately midway between said proximal and distal ends.

* * * * *